(12) United States Patent
Bonner et al.

(10) Patent No.: US 8,758,365 B2
(45) Date of Patent: Jun. 24, 2014

(54) IMPLANT SYSTEM INCLUDING GUIDING ACCESSORY AND METHODS OF USE

(75) Inventors: Matthew D. Bonner, Plymouth, MN (US); Vladimir P. Nikolski, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 190 days.

(21) Appl. No.: 13/197,156

(22) Filed: Aug. 3, 2011

(65) Prior Publication Data
US 2013/0035748 A1    Feb. 7, 2013

(51) Int. Cl.
    A61B 19/00    (2006.01)
(52) U.S. Cl.
    USPC ............. 606/129; 607/123; 607/131; 606/41
(58) Field of Classification Search
    USPC ............. 606/41, 129; 128/898–899; 607/119, 607/122–128, 131
    See application file for complete search history.

(56) References Cited

U.S. PATENT DOCUMENTS

| | | | |
|---|---|---|---|
| 3,943,936 A | 3/1976 | Rasor et al. | |
| RE30,366 E | 8/1980 | Rasor et al. | |
| 5,531,780 A * | 7/1996 | Vachon .................. | 607/120 |
| 5,902,331 A | 5/1999 | Bonner et al. | |
| 7,444,180 B2 | 10/2008 | Kuzma et al. | |
| 2004/0059404 A1 | 3/2004 | Bjorklund et al. | |
| 2004/0068312 A1* | 4/2004 | Sigg et al. ............... | 607/120 |
| 2006/0085042 A1* | 4/2006 | Hastings et al. ......... | 607/33 |
| 2006/0241732 A1 | 10/2006 | Denker et al. | |
| 2007/0088418 A1 | 4/2007 | Jacobson | |
| 2007/0150037 A1 | 6/2007 | Hastings et al. | |
| 2007/0156130 A1 | 7/2007 | Thistle | |
| 2008/0039904 A1 | 2/2008 | Bulkes et al. | |
| 2008/0249525 A1 | 10/2008 | Lee et al. | |
| 2009/0319015 A1 | 12/2009 | Horn-Wyffels | |

FOREIGN PATENT DOCUMENTS

WO    2006/099425    9/2006

OTHER PUBLICATIONS (PCT/US2012/049017) PCT Notification of Transmittal of the International Search Report and the Written Opinion of the International Searching Authority.

* cited by examiner

*Primary Examiner* — Katherine Dowe
*Assistant Examiner* — Sidharth Kapoor
(74) *Attorney, Agent, or Firm* — Reed A. Duthler

(57) ABSTRACT

A guiding accessory, for use in conjunction with a guidewire and a catheter of an implant system, facilitates passage of an elongate and flexible conductor of a relatively compact therapy delivery device to an implant site, for example, within the cardiac venous system, when a therapy generator of the device is held within a distal portion of the catheter, and the catheter, device and guiding accessory are advanced along the guidewire. The guiding accessory includes a helically extending wall that forms a lumen within which the device conductor and guidewire extend. After advancing the catheter, guiding accessory and device to the implant site, the helically extending wall is unwound from around the device conductor, for removal, preferably, by pulling proximally on a tension line, which is attached to a proximal end of the wall.

11 Claims, 6 Drawing Sheets

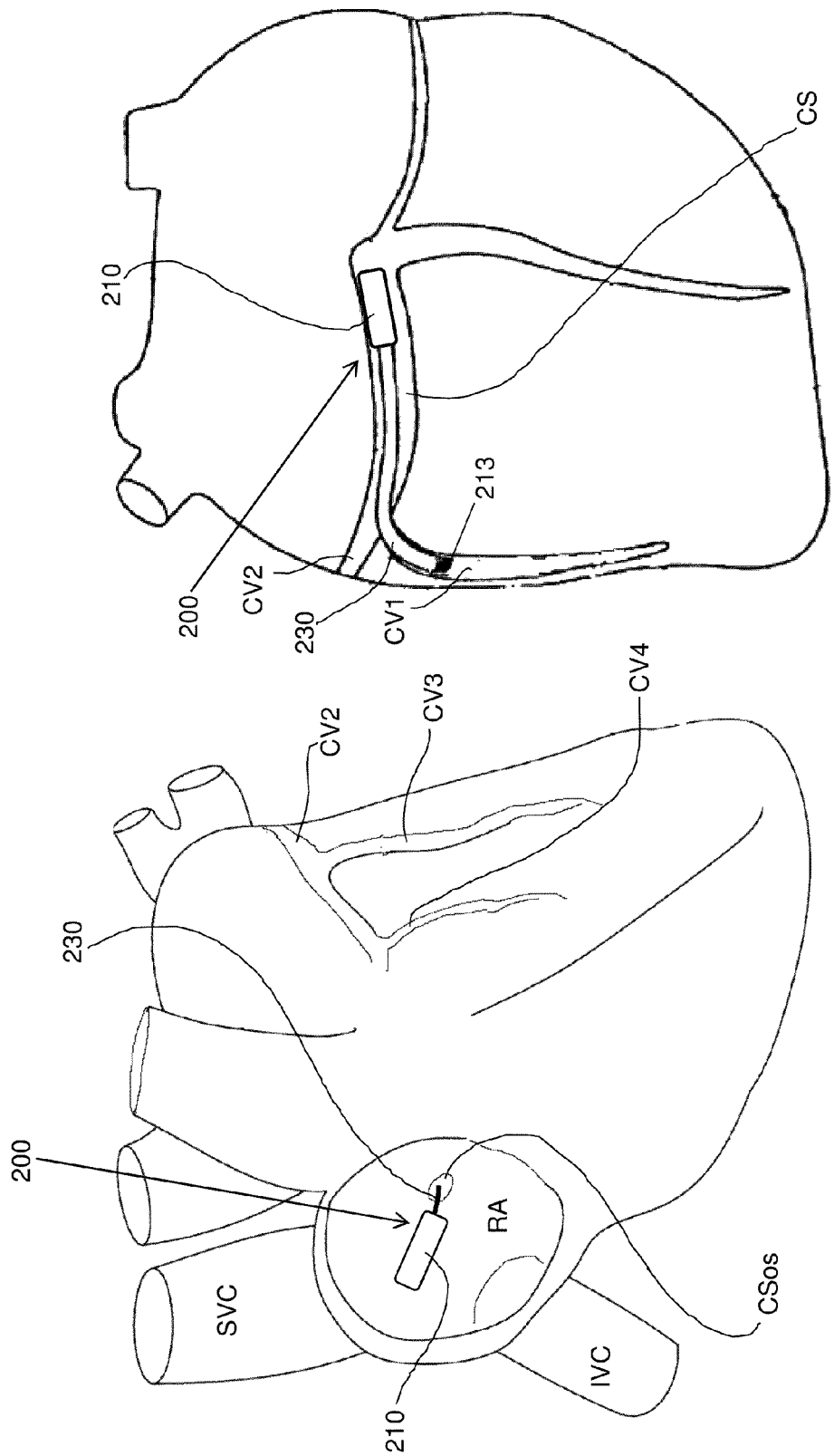

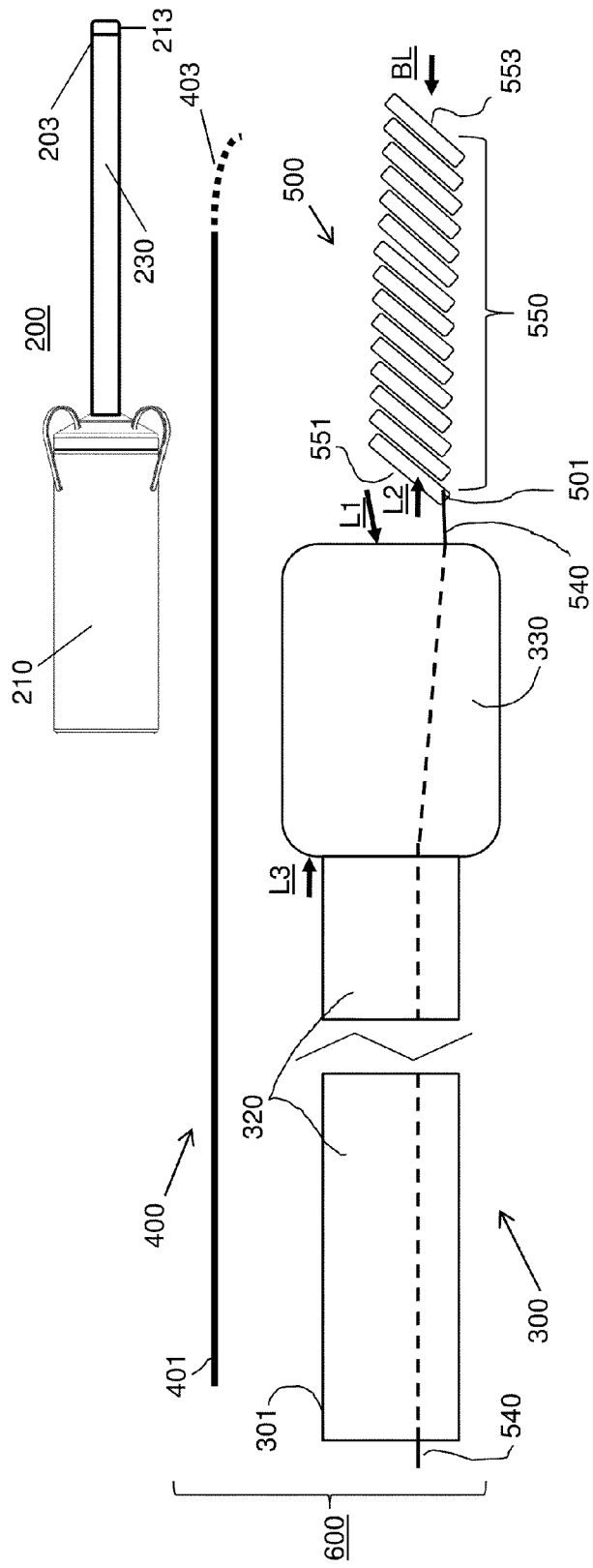
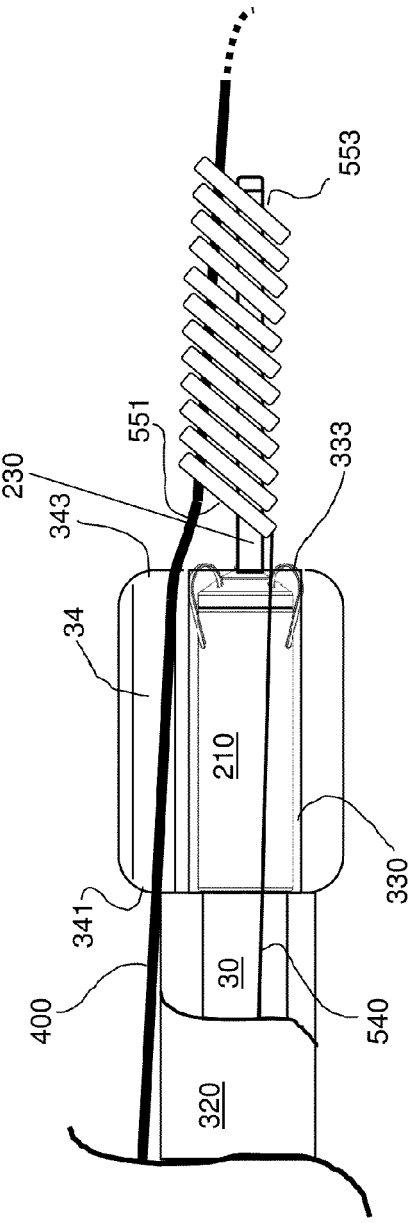
FIGURE 3A
FIGURE 3B

IMPLANT SYSTEM INCLUDING GUIDING ACCESSORY AND METHODS OF USE

TECHNICAL FIELD

The present invention pertains to systems for implanting therapy delivery devices and more particularly to guiding accessories of the systems and methods of use.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of cardiac pacing devices that are wholly contained within a relatively compact package for implant in close proximity to the pacing site, for example, within the right ventricle (RV) of the heart. With reference to FIG. 1, such a device 100 is illustrated, wherein pace/sense electrodes 111, 112 are formed on an exterior surface of a shell 101 that hermetically contains a pulse generator including pulse generator electronics and a power source. Shell 101 is preferably formed from a biocompatible and biostable metal such as titanium overlaid with an insulative layer, for example, medical grade polyurethane or silicone, except where electrode 112 is formed as an exposed portion of capsule 101. A hermetic feedthrough assembly (not shown), such as any known to those skilled in the art, couples electrode 111 to the pulse generator contained within shell 101.

FIG. 1 further illustrates a fixation member 115 mounted to an end of shell 101, in proximity to electrode 111, in order to fix, or secure electrode 111 against the endocardial surface in the apex of the RV. However, in some patients, pacing stimulation may be more effective if delivered to a right atrial site or a left ventricular site. Thus, alternative forms of relatively compact pacing devices have been developed for these alternate implant sites and there is a need for corresponding implant systems and methods.

SUMMARY

Embodiments and methods of the present invention facilitate the implant of a type of relatively compact therapy delivery device which includes an elongate and flexible isolated conductor extending from a therapy generator of the device. Methods employ a guiding accessory in conjunction with a catheter and guidewire to facilitate passage of the conductor to an implant site, for example, into the cardiac venous system via an ostium of the coronary sinus, when the therapy generator of the device is held within a distal portion of the catheter. The guiding accessory includes a helically extending wall that forms a lumen within which the conductor of the device can extend, when the generator is held within the distal portion of the generator. The catheter includes a lumen, preferably extending alongside the distal portion, for guidewire passage; and the lumen of the guiding accessory also allows passage of the guidewire, alongside the conductor of the device, so that the catheter and guiding accessory, along with the device, may be advanced along the guidewire to an implant site. After advancing the catheter, guiding accessory and device to the implant site, the helically extending wall of the guiding accessory is removed from around the conductor of the device, preferably, by pulling proximally on a tension line, which is attached to a proximal end of the helically extending wall, to draw the wall toward the distal portion of the catheter, thereby unwinding the wall from around the conductor.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIGS. 2B-C are schematics illustrating alternative sites at which the device of FIG. 2A may be implanted;

FIG. 3A is a plan view of an implant system, according to some embodiments, alongside the device of FIG. 2A;

FIG. 3B is a plan view, with partial section, of a distal portion of the implant system within which the device and a guidewire are loaded, according to some embodiments;

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
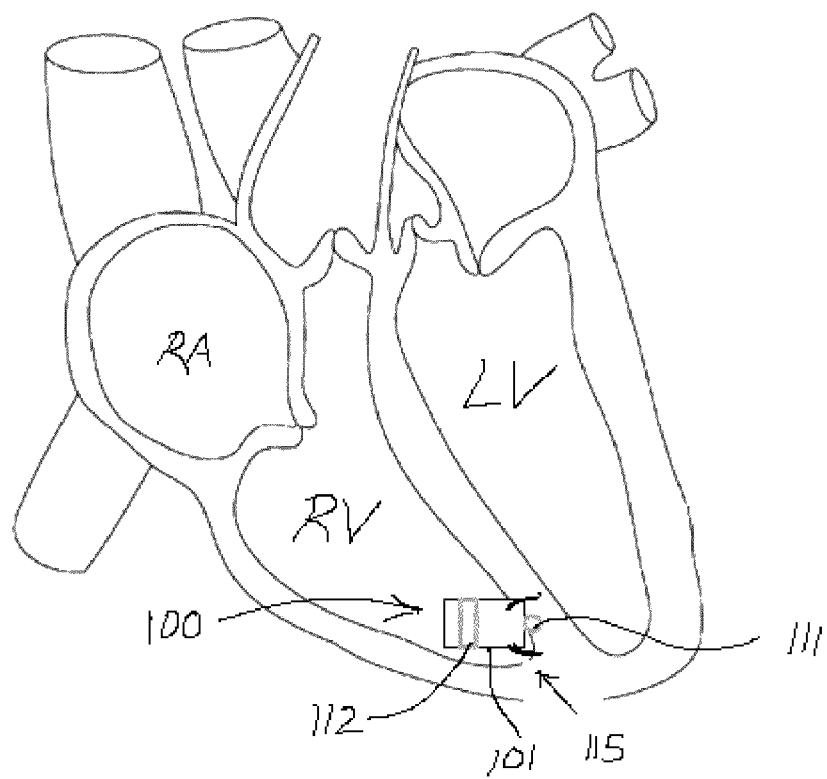
FIG. 1 is a schematic showing an example of an implanted cardiac stimulation device.
Figure 2A:
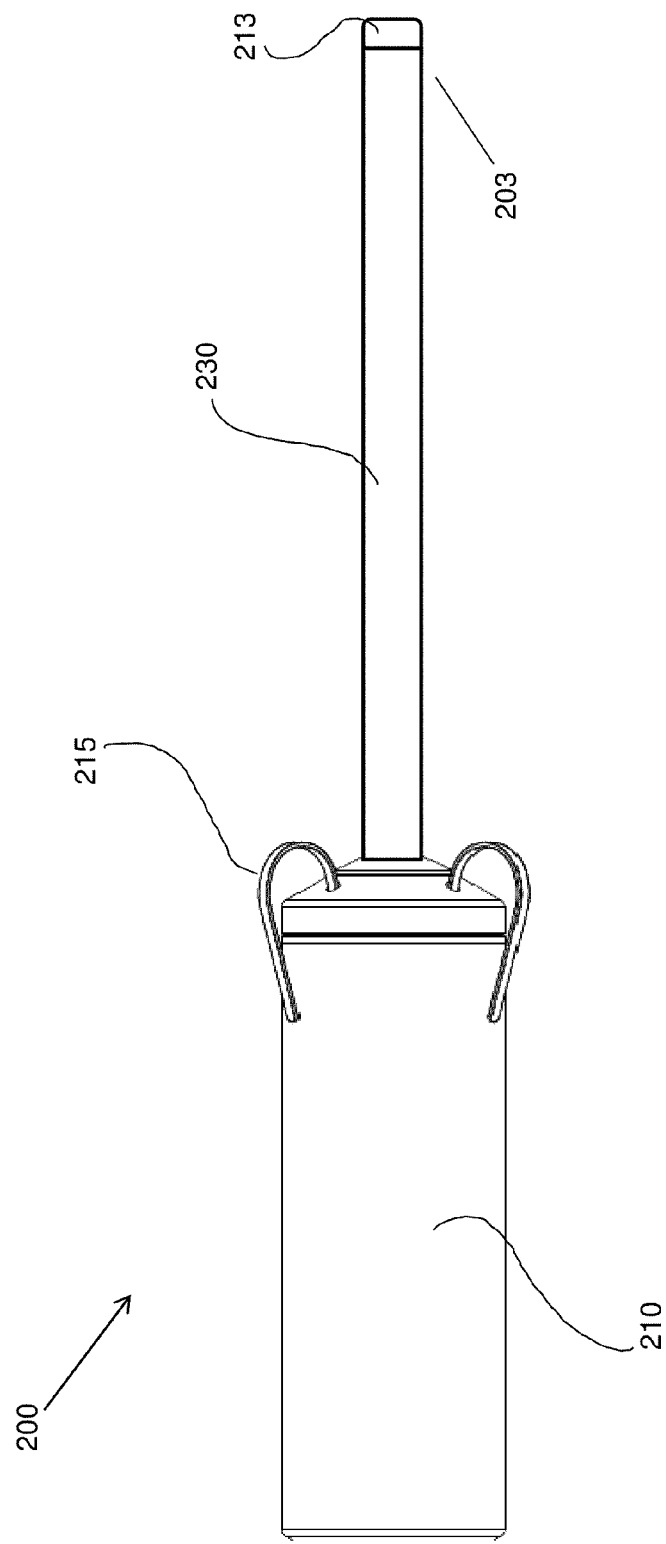
FIG. 2A is a plan view of another type of implantable therapy delivery device.

FIG. 2A is a plan view of an exemplary implantable therapy delivery device 200 for which implant methods and systems of the present invention are suitable. FIG. 2A illustrates device 200 including a therapy generator 210, a fixation member 215 coupled thereto, and a therapy delivery element 213 coupled to generator 210 via an elongate and flexible isolated conductor 230. Device 200 is preferably sized to be wholly implanted at a cardiac site, wherein exemplary dimensions are as follows: a length of generator 210 is between approximately 20 mm and approximately 25 mm; a diameter of generator 210 is between approximately 5 mm and approximately 7 mm; a length of conductor 230 is preferably between approximately 20 mm and approximately 80 mm; and a diameter of conductor 230 is preferably between approximately 0.025 inch (0.6 mm) and approximately 0.035 inch (0.9 mm). Device 200 may be adapted to deliver any type of suitable therapy, for example, device 200 may be similar to the above-described device 100 wherein generator 210 is a pacing pulse generator contained in a hermetic enclosure/shell, and therapy delivery element 213 is an electrode, albeit one that is offset from generator 210 by the length of conductor 230. With reference to FIGS. 2B-C, alternate implant sites for device 200, which are facilitated by the length of conductor 230, are shown.

FIG. 2B is an anterior view of a heart in which a portion of a right atrial wall is cut away; and FIG. 2C is a posterior view of the heart in which a portion of the coronary venous system is cut away. FIG. 2B illustrates generator 210 fixed in proximity to a coronary sinus ostium CSos within the right atrium RA, so that conductor 230 extends into ostium CSos for positioning of therapy delivery element 213 (not shown) within the coronary sinus CS, or upstream thereof, in another vein, if the length of conductor 230 allows. FIG. 2C illustrates the coronary sinus CS and a first coronary vein CV1 extending distally therefrom. In FIG. 2C, generator 210 is shown fixed within a proximal portion of the coronary sinus CS, and conductor 230 is shown extending from the coronary sinus CS so that delivery element 213 is located within vein CV1. If delivery element 213 is an electrode, the illustrated position for implant may be suitable for left ventricular pacing; alternately, for this same purpose, delivery element 213 may be positioned within any of the other coronary veins CV2, CV3, CV4 (FIG. 2B). According to methods and embodiments of the present invention an implant system, such as a system 600 shown in subsequent Figures, includes a guiding accessory 500 to facilitate delivery of device 200 to any the above-described implant locations.

FIG. 3A is a plan view of implant system 600; and FIG. 3B is a plan view of a distal portion of implant system 600 with a cut-away section. FIG. 3A illustrates device 200 alongside implant system 600, and implant system 600 including a catheter 300, a guidewire 400 and guiding accessory 500. Guidewire 400 may be any suitable type known to those skilled in the art of interventional cardiology and electro-physiology, preferably having a diameter, in proximity to a distal tip 403 thereof, of between 0.010 inch and 0.018 inch; and catheter 300 may be constructed with a fixed shape distal segment or a steerable distal segment according to construction methods known in the art. Catheter 300 is shown including an elongate shaft 320 extending from a proximal end 301 of catheter 300 to a distal portion 330 of catheter 300. FIG. 3B illustrates a lumen 30 of catheter shaft 320 opening into an interior of distal portion 330, which interior holds generator 210 of device 200. Although not shown, lumen 30 extends to proximal end 301 of catheter 300. FIG. 3B further illustrates catheter 300 including a guidewire lumen 34, which, preferably, only extends approximately along a length of distal portion 330. However, according to some alternate embodiments, guidewire lumen 34 may extend further proximally, along catheter shaft 320, or may extend within catheter shaft 320, alongside lumen 30, and open into the interior of distal portion 330. FIGS. 3A-B further illustrate guiding accessory 500 including a helically extending wall 550 and a tension line 540 attached to wall 550; tension line 540 extends proximally from wall 550 and into distal portion 330 of catheter 300, then along a length of catheter shaft 320 and out proximal end 301 of catheter 300. Tension line 540 is preferably formed from a relatively high tensile strength polymer fiber, such as polyester, which is attached, for example, by tying with a knot to a proximal end 501 of wall 550. According to the illustrated embodiment, tension line 540 is preferably accommodated within lumen 30 along the length of shaft 320. According to some additional embodiments, lumen 30 may accommodate both tension line 540 and guidewire 400, so that lumen 34 is not necessary.

Figure 4:
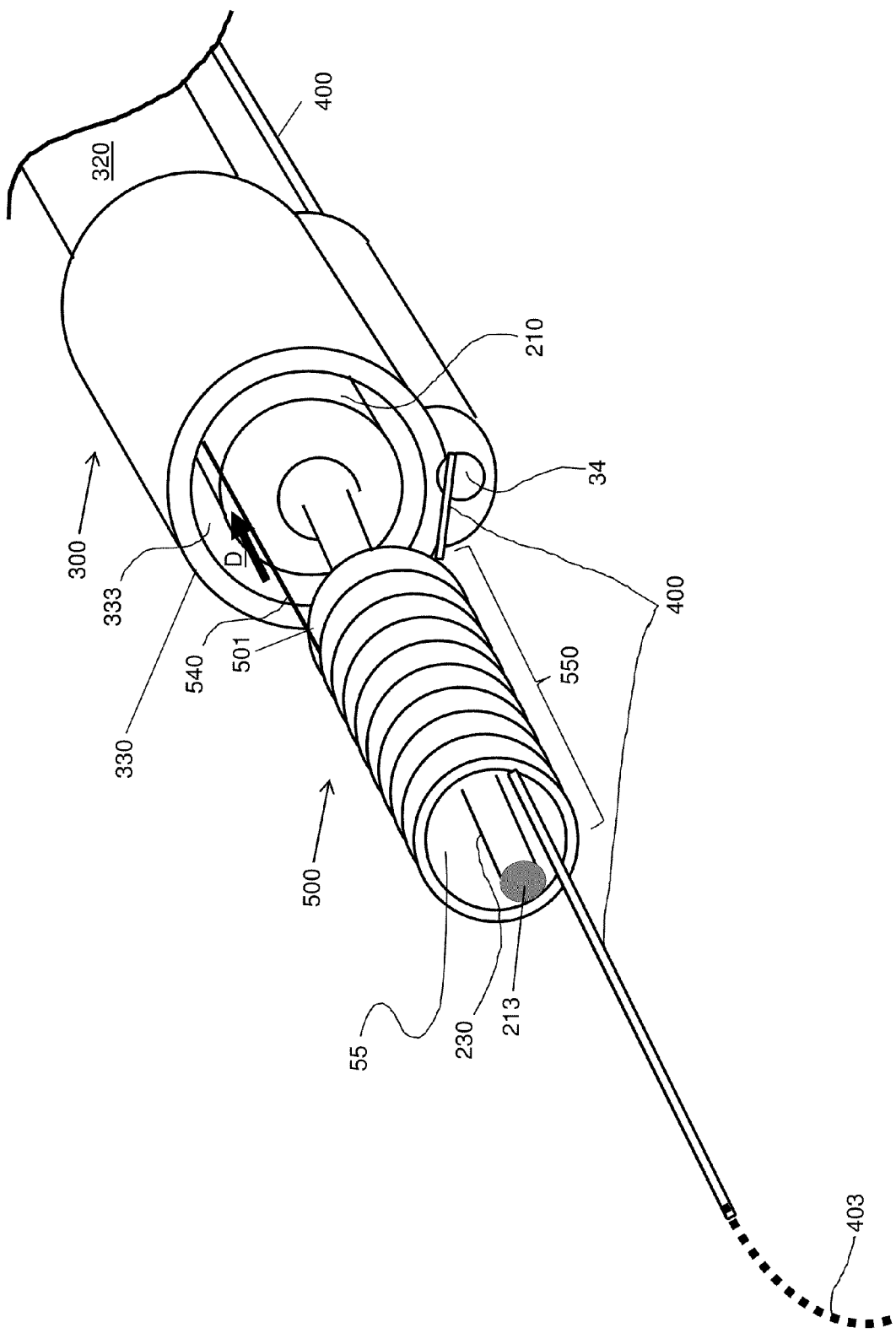
FIG. 4 is a perspective view of the distal portion of FIG. 3B.

With further reference to FIGS. 3A-B, generator 210 of device 200 may be loaded into distal portion 330 of catheter 300, through a distal opening thereof, per arrow L1, and a distal end 203 of elongate and flexible isolated conductor 230 may be loaded into a lumen 55 (FIG. 4), which is formed by helically extending wall 550 of guiding accessory 500, through a proximal opening 551 thereof, per arrow L2. Either before or after loading device 200, guidewire 400 may be loaded into lumen 34 of catheter and into lumen 55 of guiding accessory 500, for example, per arrows L3 and L2, respectively. Thus, lumen 55 has a diameter sized to accommodate therein guidewire 400 and conductor 230 of device 200, side-by-side, as shown in FIGS. 3B and 4; and guidewire 400 is slidable alongside conductor 230 within lumen 55. Furthermore, the size of lumen 55 allows helically extending wall 550 and conductor 230 to move together along guidewire 400. Helically extending wall 550 may be formed from a coiled strip of one or a combination of a resilient biocompatible polymer and a resilient biocompatible metal, wherein the strip preferably has a rectangular cross-section or a round cross-section. Alternately, wall 550 may be formed from a spiral cut polymer tube. A thickness of wall 550 is preferably between approximately 0.007 inch (0.2 mm) and approximately 0.02 inch (0.5 mm), according to some embodiments. Adjacent turns of wall 550 are separable from one another so that, when a pull force is applied, for example, to proximal end 501, via tension line 540, wall 550 unwinds, as will be described in greater detail below.

Figure 5:
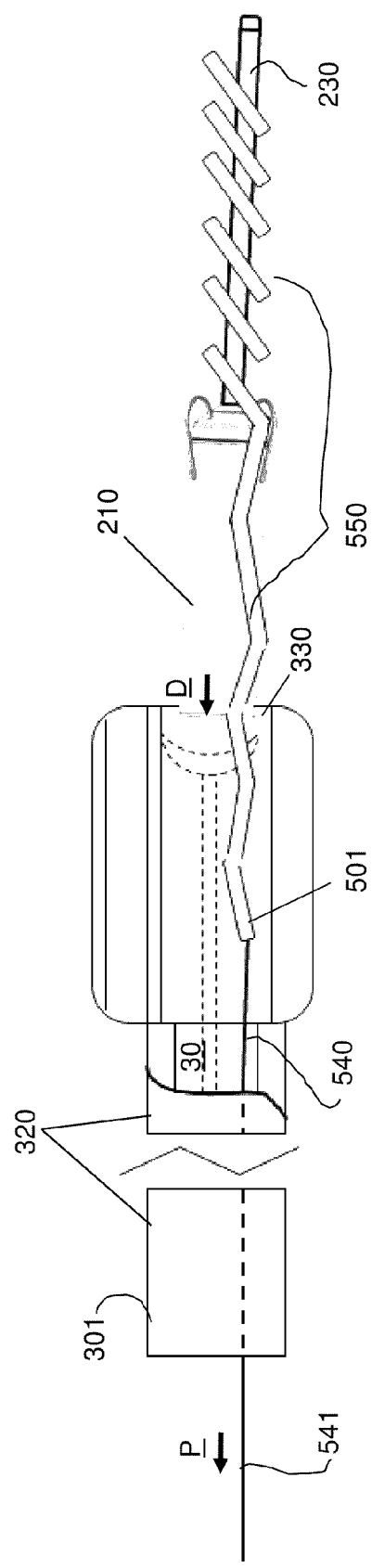
FIG. 5 is a plan view, with partial section, of the implant system wherein a guiding accessory thereof is shown being removed, according to some methods and embodiments.

According to some methods of the present invention, after using guidewire maneuvering techniques, known to those skilled in the art, to advance a distal tip 403 of guidewire 400 transvenously, from a percutaneous entry site and ahead of catheter 300 and guiding accessory 500, to the right atrium RA (FIG. 2B) and into the coronary sinus CS to a location in proximity to a target implant site, catheter 300 and guiding accessory 500, with device 200 loaded therein, are advanced along guidewire 400 to the implant site, for example, as illustrated in FIG. 4. According to some alternate methods, guidewire 400 is advanced transvenously to the implant site, independent of catheter 300, device 200 and accessory 500, and then proximal end 401 of guidewire 400 is back-loaded, per arrow BL (FIG. 3A), into guiding accessory lumen 55, via a distal opening 553 thereof, and then into guidewire lumen 34, via a distal opening 343 thereof (FIG. 3B), and then out a proximal opening 341 of guidewire lumen 34, before catheter 300, accessory 500 and loaded device 200 are advanced thereover to the implant site. With reference to the implant sites illustrated by FIGS. 2B-C, it may be appreciated that, when distal portion 330 of catheter, which holds generator 210, is advanced within the proximity of the coronary sinus ostium CSos, guiding accessory 500 is useful in holding conductor 230 alongside guidewire 400 to facilitate passage of conductor 230 into the coronary sinus CS and, if necessary (dependent upon the target site for therapy delivery element 213 of device 200), upstream to one of veins, for example, CV1, CV2, CV3 or CV4. Once therapy delivery element 213 is positioned at the target site, guiding accessory 500 is removed by drawing a proximal end 501 of helically extending wall 550 toward distal opening 333 of distal portion 330 and proximally therefrom, per arrow D of FIG. 4, thereby unwinding wall 550 from around conductor 230 of device 200, for example, as shown in FIG. 5.

According to the embodiment shown in FIG. 5, tension line 540 of guiding accessory 500 is employed to unwind helically extending wall 550, by applying a pull force, for example, from a proximal end 541 of line 540, per arrow P; the unwound wall 550 is subsequently drawn into the same lumen 30 that accommodates tension line 540. According to alternate methods of the invention, other means may be employed to draw in proximal end 501 of wall 550 per arrow D, thereby unwinding wall 550 from around conductor 230; for example, a hooked wire or opposing jaws may be deployed from catheter 300 to engage proximal end 501 of wall 550 and draw it into catheter 300. With further reference to FIG. 5, dashed lines show an optional push member that may be used to push generator 210 out from distal portion 330 of catheter just prior to, or, preferably, in conjunction with, drawing proximal end 501 of helically extending wall 550 in, per arrow D. It should be noted that, although FIG. 5 shows guidewire 400 having been removed from lumen 34 of catheter 300 and from lumen 55 of guiding accessory 500 (i.e. pulled back from the implant site), according to alternate methods, guidewire 400 may remain within both lumens 34, 55 while wall 550 of guiding accessory 500 is unwound and removed, or guidewire 400 may be pulled out from lumen 55, but remain in lumen 34, while wall 550 is unwound and removed.

In the foregoing detailed description, the invention has been described with reference to specific embodiments. However, it may be appreciated that various modifications and changes can be made without departing from the scope of the invention as set forth in the appended claims.

We claim:

1. A system comprising a guidewire, a catheter, a therapy delivery device, and a guiding accessory for implanting the therapy delivery device; the device including a therapy generator, a therapy delivery element, and an elongate and flexible isolated conductor coupling the therapy generator to the therapy delivery element; the catheter including a lumen sized to accommodate passage of the guidewire and a distal portion sized to hold the therapy generator of the device, the distal portion having a distal opening through which the elongate and flexible isolated conductor of the device extends outside of, and generally distal of the distal portion, when the distal portion holds the therapy generator; and the guiding accessory comprising:
   a helically extending wall forming a lumen that extends along a length from a proximal opening thereof to a distal opening thereof, the lumen having a diameter sized to accommodate therein the guidewire and the elongate and flexible isolated conductor of the device, side-by-side, such that the guidewire is slidable within the lumen alongside the conductor, and such that the wall and the conductor together are moveable along the guidewire; and
   a tension line attached to a proximal end of the wall, the tension line having a length that is greater than a length of the implant catheter; and
   wherein adjacent turns of the helically extending wall are separable from one another so that, upon application of a pull force through the tension line, in a proximal direction, when the conductor of the device extends within the lumen, the wall unwinds from around the conductor.

2. The system of claim 1, wherein the lumen of the catheter extends alongside the distal portion thereof and includes a proximal opening and a distal opening, both located in proximity to the distal portion.

3. The system of claim 1, wherein the catheter includes another lumen and the tension line of the guiding accessory extends within the other lumen.

4. The system of claim 3, wherein the other lumen opens into the distal portion of the catheter, and the tension line extends alongside the therapy generator of the device, when the distal portion holds the therapy generator.

5. The system of claim 3, wherein the other lumen is sized to receive the helically extending wall of the guiding accessory as the pull force is applied through the tension line to unwind the wall.

6. The system of claim 1, wherein the helically extending wall of the guiding accessory is formed from a spiral-cut polymer tube.

7. The system of claim 1, wherein the helically extending wall of the guiding accessory is formed from a coiled strip of one or a combination of: a resilient polymer and a resilient metal.

8. A therapy delivery device and a guiding accessory for use in conjunction with a guidewire, and a catheter to facilitate passage of a portion of the therapy delivery device to an implant site; the device including a therapy generator, a therapy delivery element, and an elongate and flexible isolated conductor coupling the therapy generator to the therapy delivery element; the catheter including a distal portion sized to hold
the therapy generator of the device, the distal portion having an opening through which the elongate and flexible isolated conductor of the device extends outside of, and generally distal of, the distal portion, when the distal portion holds the therapy generator; and the guiding accessory comprising:
   a helically extending wall forming a lumen that extends along a length from a proximal opening thereof to a distal opening thereof, the lumen having a diameter sized to accommodate therein the guidewire and the elongate and flexible isolated conductor of the device, side-by-side, such that the guidewire is slidable within the lumen alongside the isolated conductor, and such that the wall and the conductor together are moveable along the guidewire; and
   a tension line attached to a proximal end of the helically extending wall, the tension line having a length that is greater than a length of the implant catheter; and
   wherein adjacent turns of the helically extending wall are separable from one another so that, upon application of a pull force to the tension line, in a proximal direction, when the conductor of the device extends within the lumen, the wall unwinds from around the conductor.

9. The accessory of claim 8, wherein the helically extending wall is formed from a spiral-cut polymer tube.

10. The accessory of claim 8, wherein the helically extending wall is formed from a coiled strip of one or a combination of: a resilient polymer and a resilient metal.

11. The accessory of claim 8, wherein the tension line is sized to pass within another lumen of the catheter.

* * * * *